(12) United States Patent
Van Furth et al.

(10) Patent No.: US 11,771,897 B2
(45) Date of Patent: Oct. 3, 2023

(54) SYSTEM, METHOD AND CATHETER FOR PITUITARY AND BRAIN IMPLANTATION

(71) Applicant: ACADEMISCH ZIEKENHUIS LEIDEN (H.O.D.N. LUMC), Leiden (NL)

(72) Inventors: Wouter R. Van Furth, Leiden (NL); Nienke R. Biermasz, Leiden (NL); Amir H. Zamanipoor Najafabadi, Leiden (NL)

(73) Assignee: ACADEMISCH ZIEKENHUIS LEIDEN (H.O.D.N. LUMC), Leiden (NL)

( * ) Notice: Subject to any disclaimer, the term of this patent is extended or adjusted under 35 U.S.C. 154(b) by 638 days.

(21) Appl. No.: 16/764,127

(22) PCT Filed: Nov. 14, 2018

(86) PCT No.: PCT/NL2018/050765
§ 371 (c)(1),
(2) Date: May 14, 2020

(87) PCT Pub. No.: WO2019/098830
PCT Pub. Date: May 23, 2019

(65) Prior Publication Data
US 2020/0276441 A1     Sep. 3, 2020

(30) Foreign Application Priority Data

Nov. 14, 2017 (NL) .................................. 2019909

(51) Int. Cl.
*A61N 1/36* (2006.01)
*A61M 25/00* (2006.01)
(Continued)

(52) U.S. Cl.
CPC ........ *A61N 1/3605* (2013.01); *A61M 25/0021* (2013.01); *A61M 25/0133* (2013.01);
(Continued)

(58) Field of Classification Search
CPC ............... A61N 1/0534; A61N 1/3605; A61M 25/0021; A61M 25/0133;
(Continued)

(56) References Cited

U.S. PATENT DOCUMENTS 8,549,732 B2 * 10/2013 Burg ...................... A61B 34/20
336/200
8,568,399 B2 * 10/2013 Azamian .............. A61K 31/395
606/41

(Continued)

*Primary Examiner* — Christopher A Flory
(74) *Attorney, Agent, or Firm* — NIXON PEABODY LLP; Ronald I. Eisenstein; Nicole D. Kling

(57) ABSTRACT

The present invention relates to a system, its catheter and its method for providing electrical pulses and/or therapeutic or diagnostic liquids directly to a pituitary gland of a mammal. The catheter, containing an electrode or a microcannula or both, is moved through an endovascular route of a patient to his/her sinus cavernosus and then the distal end of the electrode or microcannula is moved through an opening in the distal end of the catheter and then through a perforation in the medial wall of the sinus cavernosus, to the pituitary gland.

20 Claims, 16 Drawing Sheets

(51) Int. Cl.
  *A61M 25/01* (2006.01)
  *A61N 1/05* (2006.01)
(52) U.S. Cl.
  CPC ... *A61N 1/0534* (2013.01); *A61M 2025/0042* (2013.01); *A61M 2025/0166* (2013.01); *A61M 2210/0693* (2013.01)
(58) Field of Classification Search
  CPC .. A61M 2025/0042; A61M 2025/0166; A61M 2025/0693
  See application file for complete search history.

(56) References Cited

U.S. PATENT DOCUMENTS

| | | | |
|---|---|---|---|
| 8,764,709 B2* | 7/2014 | Chang | A61B 17/12104 |
| | | | 604/509 |
| 9,308,361 B2* | 4/2016 | Muni | A61B 17/3417 |
| 9,717,442 B2* | 8/2017 | Jacobsen | A61B 5/061 |
| 2005/0101909 A1 | 5/2005 | Rossi | |
| 2007/0255379 A1* | 11/2007 | Williams | A61N 1/05 |
| | | | 607/116 |
| 2010/0241155 A1 | 9/2010 | Chang et al. | |
| 2013/0018303 A1 | 1/2013 | Webster et al. | |
| 2014/0018788 A1* | 1/2014 | Engelman | A61B 18/1492 |
| | | | 606/33 |
| 2014/0236207 A1 | 8/2014 | Makower et al. | |
| 2015/0257779 A1* | 9/2015 | Sinelnikov | A61N 7/022 |
| | | | 606/28 |
| 2016/0029916 A1* | 2/2016 | Putz | A61B 5/291 |
| | | | 600/378 |
| 2016/0302682 A1* | 10/2016 | Lieber | G01N 27/4146 |
| 2016/0338724 A1* | 11/2016 | Sinelnikov | A61M 25/09 |
| 2016/0374710 A1* | 12/2016 | Sinelnikov | A61B 17/3207 |
| | | | 600/439 |

* cited by examiner

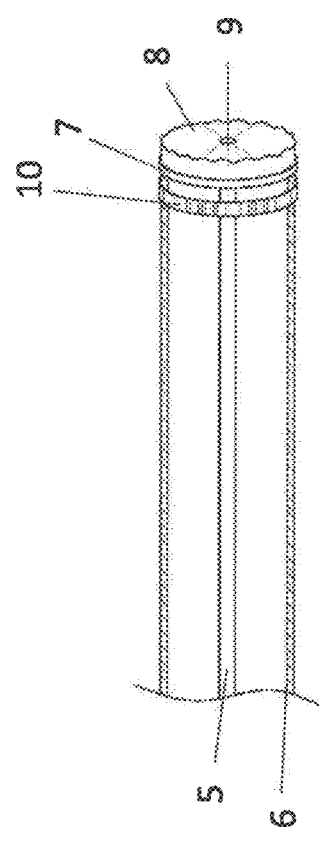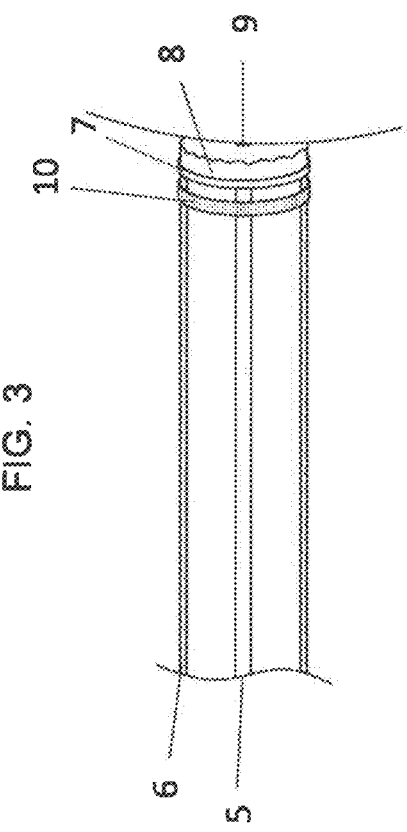
FIG. 3
FIG. 4

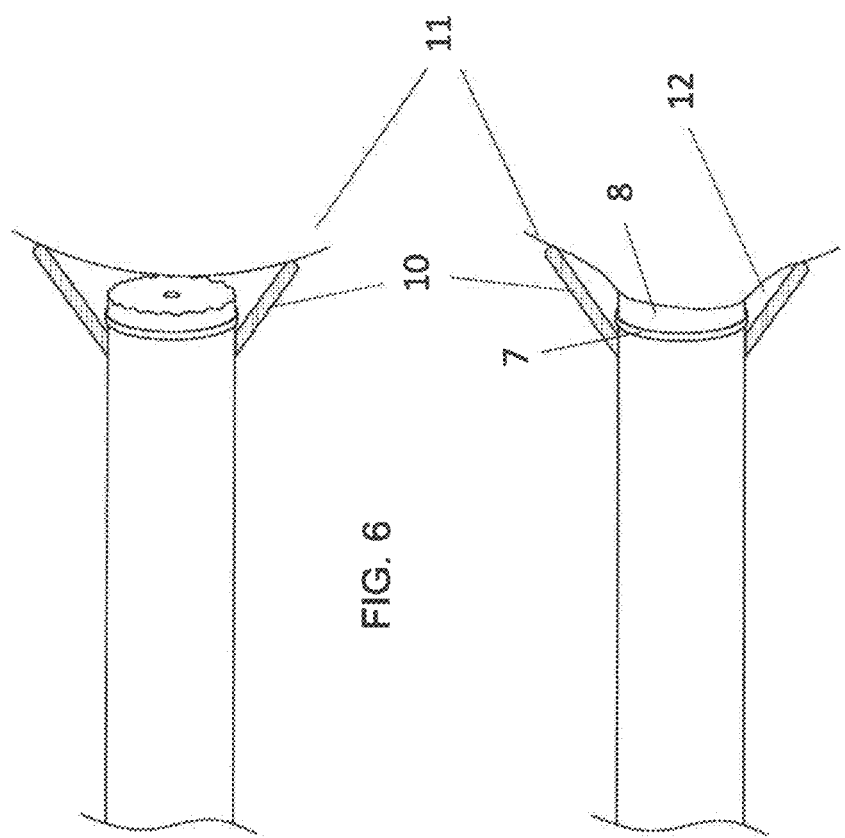

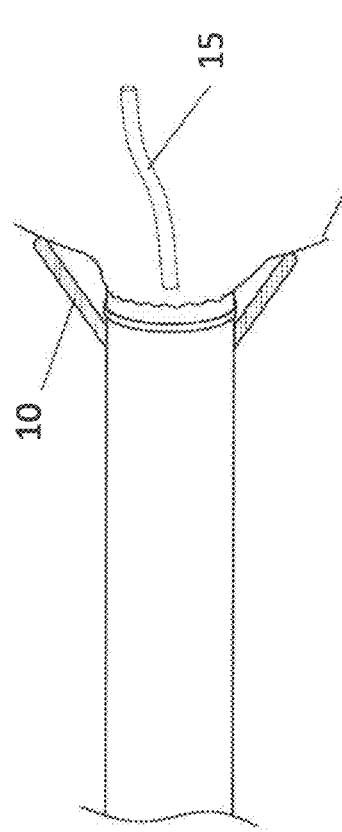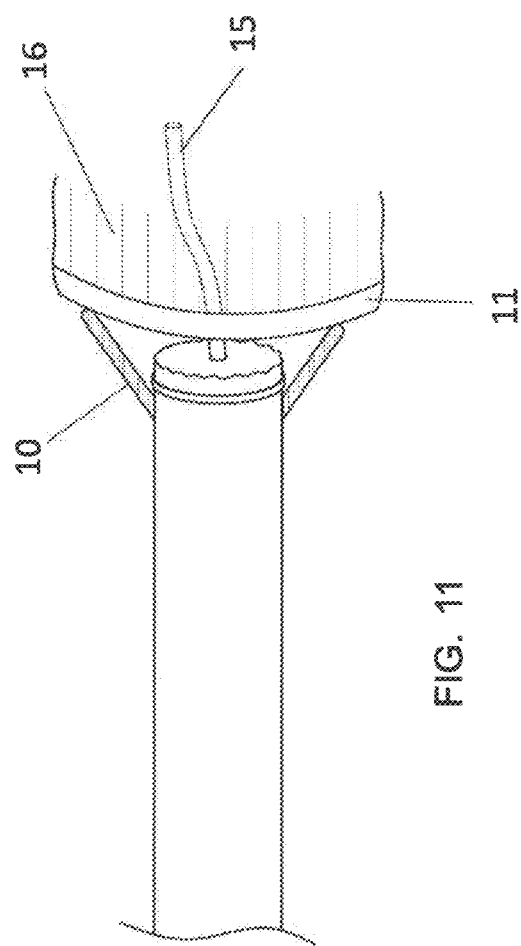
FIG. 10
FIG. 11

SYSTEM, METHOD AND CATHETER FOR PITUITARY AND BRAIN IMPLANTATION

CROSS-REFERENCE TO RELATED APPLICATIONS

This application is a 35 U.S.C. § 371 National Phase Entry Application of International Application No. PCT/NL2018/050765 filed Nov. 14, 2018, which claims benefit under 35 U.S.C. § 119(b) of NL Application No. 2019909 filed Nov. 14, 2017, the contents of which are incorporated herein by reference in their entireties.

FIELD OF THE INVENTION

The present invention relates to a system for endovascular implantation of a catheter within a mammal body. The present invention particularly relates to a system for endovascular implantation of a catheter supplying electrical energy or therapeutic or diagnostic fluids or materials, such as stem cells, particularly to the pituitary gland, pituitary stalk, basal ganglia and/or hypothalamus of the brain.

BACKGROUND OF THE INVENTION

It is known to implant a catheter, containing an electrode coupled to a source of electrical pulses, directly in a patient's brain, through the cerebral cortex, to modify their activity by deep brain stimulation. This can give relief to the symptoms of, for example, Parkinson's disease, depression and compulsive disorders. The catheter can also contain a tube for injecting a therapeutic or diagnostic liquid directly in the brain or neurological tissue to modify their activity, see for instance U.S. Pat. No. 7,505,807B1 and U.S. Pat. No. 8,116,883B2. Similarly, hormonal activity of glands, such as the pituitary, thymus and adrenal glands can be modified, using such a catheter to provide electrical pulses and/or therapeutic or diagnostic liquids directly to the glands, see for instance U.S. Pat. No. 8,515,542B2 and US2008065002A1.

However, it has been a particularly difficult problem to provide electrical pulses and/or therapeutic or diagnostic liquids with a catheter directly to the pituitary gland, or to the pituitary stalk and hypothalamus via the pituitary gland. This is because the catheter has had to be inserted in the pituitary gland through the sphenoid sinus (the airy nasal cavity that is located before/under the sella) of the patients. The pituitary gland, which is in the sella, is separated from the sphenoid sinus by a layer of the dura mater (hard brain membrane), bone and mucous membrane of the nasal cavity. Providing electrical pulses and/or therapeutic or diagnostic liquids to the pituitary gland through the sphenoid sinus has therefore been difficult because the catheter has had to be inserted through the hard brain membrane, bone and mucous membrane of the nasal cavity. Also, the catheter has had to be inserted through the patient's nose which has posed a significant infection risk to the patient, as described for instance in U.S. Pat. No. 5,735,817 A.

Furthermore, the catheter has had to be connected to a regulating device, which is approachable for maintenance and adjustment. Therefore, the catheter has had to be guided outside the nasal cavity to a suitable place for connection. A catheter coming out a person's nostril has been unappealing and has had a risk of easy dislocation. Therefore, the catheter has had to again be placed through mucous membrane and bone to enter a subcutaneous space in the face, from which it can be guided to the stimulating device.

Because of the importance of the pituitary gland (which is the central hormone gland of the brain through which essential body functions, such as menstrual cycle, stress response, and paediatric growth are regulated), an alternative system has been sought for providing electrical pulses and/or therapeutic or diagnostic liquids and materials with a catheter directly to the pituitary gland and from there to the pituitary stalk (which is the connection between the hypothalamus and the pituitary) and the hypothalamus (which is a portion of the brain that links the nervous system to the endocrine system via the pituitary gland).

SUMMARY OF THE INVENTION

This invention relates to a system for providing electrical pulses and/or therapeutic or diagnostic liquids directly or indirectly to a pituitary gland of a mammalian patient or to a pituitary stalk or to a hypothalamus of the mammalian patient via the pituitary gland, using a catheter that has a distal end movable distally through blood vessels, in an endovascular route, of the mammal and then into and through a sinus cavernosus of the mammal and that contains an action member, a distal end of which is movable distally within an elongated hollow tube of the catheter, the system being characterized by comprising, as an action member, an electrode and/or a microcannula having a distal end that can move:

distally, within the hollow tube of the catheter, through the endovascular route and then into and through the sinus cavernosus; and then distally out of the catheter through an opening in the distal end of the catheter and then through a perforation in a medial wall of the sinus cavernosus to the pituitary gland and then to and into or under or around the pituitary gland;

wherein the system is capable of actively bending the hollow tube of the catheter to a predetermined angle of no less than 75° when moving along the endovascular route. Advantageously, the angle is at least 80°, more advantageously at least 85°, yet more advantageously at least 90°.

Advantageously, the system is operable to move the distal end of the action member, within the hollow tube of the catheter, via the endovascular route from a vena jugularis of the mammal, to an inferior or superior petrosal sinus of the mammalian patient, and then to the sinus cavernosus of the mammalian patient. More advantageously, the distal end of the catheter moves via the endovascular route from the ileac vein or femoral vein in a groin or the cephalic vein in the arm of the mammalian patient where the catheter is inserted in the mammalian patient.

Also advantageously, the catheter of the system comprises an exterior lumen within the hollow tube of the catheter and an interior lumen within the exterior lumen, the exterior lumen containing a first steering mechanism and the interior lumen containing a second steering mechanism, and the first and second steering mechanisms being operable to actively bend the hollow tube to a predetermined angle of no less than 75°.

Also advantageously, the catheter of the system has an action member comprising a push wire having a distal end that can move:

distally, within the hollow tube of the catheter, through the endovascular route and then into and through the sinus cavernosus; and then;

distally out of the catheter through the opening in the distal end of the catheter and then through the perforation in the medial wall of the sinus cavernosus. More advantageously, the distal end of the push wire comprises a tip containing a sharp, advantageously pointed, element that can be projected distally from the opening in the distal end of the catheter to form the perforation in the medial wall of the cavernous sinus.

Also advantageously, a distal-most part of the catheter of the system includes a malleable cushion to allow good contact of the distal-most part with the surface of the medial wall of the sinus cavernosus. Also advantageously, the exterior of a distal part of the catheter, advantageously between the collar and the cushion, has a radiopaque ring that can be recognized, and made visible, by an imaging device, such as an X-ray, fluoroscopy, angiogram, MRI or a CT-scan device to facilitate proper positioning of the distal part of the catheter in the patient. (This visibility or recognition ability is further referred to herein as "radiopacity"). Additionally or alternatively, a distal part of the catheter, advantageously between the collar and the cushion, contains one or more electromagnetic localizers to facilitate proper positioning of the distal part in the patient. Each localizer is part of a tracking system, in which the localizer includes a transmitter and receiver coil array, enabling it to transmit electromagnetic signals and receive electromagnetic energy from a transmitter coil array. The transmitter coil can suitably be located in, or adjacent to, the patient and can generate an electromagnetic field to energize each localizer.

Also advantageously, the exterior of the distal end of the catheter of the system, adjacent to, and proximal of, the cushion, has an annular collar that can be inflated, so that distal surfaces of the collar are projected distally from the distal end of the catheter around the perforation in the medial wall of the cavernous sinus to close a space around the opening in the distal end of the catheter between the distal end of the catheter and the perforation, advantageously before the tip of the push wire is projected distally from the opening in the distal end of the catheter to form the perforation in the medial wall of the cavernous sinus. More advantageously, the exterior of the distal end of the catheter, adjacent to, and proximal of, the inflatable annular collar, also has a stabilizing device, to secure the position of the distal end of the catheter within the perforation in the medial wall of the sinus cavernosus, without occluding the perforation, the stabilizing device comprising an inflatable tripod, provided circumferentially about the exterior of the catheter and having inflatable, radially extendable legs.

Also advantageously, the catheter of the system comprises a third steering mechanism comprises guide wire within the hollow tube for pivoting or steering the distal end of the catheter in a desired direction, advantageously by remote control, for controlling its distal movement through the endovascular route and then into and through the sinus cavernosus.

Also advantageously: the catheter of the system has an action member comprising an electrode, the distal end of which has one or more contact points for electrical stimulation of endocrine tissue of the pituitary gland, the pituitary stalk or the hypothalamus; and/or the one or more action members comprise a microcannula, the distal end of which has one or more central or wall-located hollow channels, each with one or more side openings, through which small volumes of a fluid or gel can flow into the pituitary gland, the pituitary stalk or the hypothalamus, still more advantageously with side openings that can be opened and closed by remote control. Advantageously, the electrode comprises one or more penetrating electrodes, one or more surface area electrodes, or a combination of both. More advantageously, the electrode design and electrode placement is such that a focal electrical field is generated.

The electrode is advantageously adapted to: electrically stimulate the pituitary gland to produce and secrete adrenocorticotropic hormone (ACTH) and/or alpha-melanocyte stimulating hormone (MSH) and/or oxytocin; and/or electrically stimulate the pituitary gland to stimulate the magnocellular nuclei of the anterior hypothalamus through axons that descend through the pituitary stalk to the pituitary gland. Also more advantageously, distal portions of the electrode or microcannula or both have a form memory and thus can form a three-dimensional shape, such as a circle, oval or helix, within or about the pituitary gland, advantageously when triggered by remote control. Still more advantageously, distal portions of the electrode, when inserted in the pituitary gland, have a coil shape within the pituitary gland.

Also advantageously, the catheter of the system, particularly its hollow tube, has a peel-away configuration, so that an electrode or microcannula can subsequently be removed from the patient through the catheter in such a way, that the electrode or microcannula remains intact.

This invention also relates a catheter, advantageously the catheter of the system of the invention, for providing electrical pulses and/or therapeutic or diagnostic liquids directly to a pituitary gland of a mammal or to a pituitary stalk or to a hypothalamus of the mammal via the pituitary gland, a distal end of the catheter containing one or more action members, a distal end of each of which can move distally in the catheter via blood vessels of an endovascular route of the mammal and then via a sinus cavernosus of the mammal to a medial wall of the cavernous sinus; the catheter being characterized by: the one or more action members comprising a push wire having a distal end having a tip with a sharp, advantageously pointed, element that can be projected distally from an opening in the distal end of the catheter to form a perforation in the medial wall of the cavernous sinus, through which: a distal end of another action member, advantageously an electrode or a microcannula or both can be moved distally through the cavernous sinus and the electrode and/or microcannula can then be inserted in, or under/around the pituitary gland from the distal end of the catheter.

This invention further relates to a method for providing electrical pulses and/or therapeutic or diagnostic liquids directly to a pituitary gland of a mammal or to a pituitary stalk or to a hypothalamus of the mammal via the pituitary gland, comprising the steps of:

moving a distal end of a catheter, advantageously the catheter of the system of this invention, that contains one or more action members, a distal end of each of which is movable distally within the catheter, through an endovascular route of the mammal from a vena jugularis of the mammal, to an inferior or superior petrosal sinus of the mammal, and then to a sinus cavernosus of the mammal; and then
  perforating a medial wall of the cavernous sinus to the pituitary gland; and then
  moving the distal end of the one or more action members distally from the catheter, through an opening in the distal end of the catheter and through the perforated medial wall of the sinus cavernosus, to the pituitary gland.

Advantageously, the distal end of each of the one or more action members moves via the endovascular route from the ileac vein or femoral vein in a groin or the cephalic vein in the arm of the mammal where the catheter is inserted in the mammal.

This invention yet further relates to a method of treating endocrinological medical conditions related to the components of the endocrine system such as the adrenal glands, pituitary gland, and hypothalamus with the system and the catheter of this invention. Non-limiting examples of such endocrinological conditions include hypoglycemia, diabetes type I and II, obesity, hyperthyroidism, hypothyroidism, amenorrhea, dysmenorrhea, infertility, impotence, anorgasmia, delayed orgasm, perimenstrual syndrome, hypercholesterolemia, hypertriglycridinemia, Cushing's disease, Addison's disease, Addison's crisis, malabsorption syndrome, dysautonomia, chronic fatigue syndrome, fatigue, heat exhaustion, cold extremities, hot flashes, vasomotor instability, Raynaud's syndrome, hormonal disorders, metabolic disorders such as gout, disorders of metabolism and metabolic storage diseases where there is an accumulation of abnormal amounts of various substances such as glycogen in glycogen storage diseases, iron in hemochromatosis or copper in Wilson's disease, auto-immune disorders, sleep disorders and disruptions in the circadian rhythm. In particular, the invention relates to the treatment of Adison's disease and Adison's crisis.

Typical treatment for Adison's disease involves replacing the absent hormones by administration of a corticosteroid such as hydrocortisone and fludrocortisone, which needs to be applied in relatively large amounts, and potentially requiring a lifelong, continuous steroid replacement therapy, with regular follow-up treatment and monitoring for other health problems. In the case of a crisis, an injection of corticosteroid is usually required. Without treatment, an adrenal crisis can result in death.

However, the treatment method of this invention now permits triggering of the patient's own production of steroid hormones by triggering the feedback loop in the patient's own pituitary gland, or even the patient's hypothalamus, e.g., by in situ administration of CRH or a useful analogue thereof, or a combination of CRH with other pharmacologically active components like vasopressin, or focal electrical stimulation.

This invention still further relates to a method of treating, with the system and the catheter of this invention, pain, pain perception, post-traumatic stress disorder, epilepsy, depression, anxiety disorders, and other similar conditions through stimulation of the posterior lobe of the pituitary gland, the intermediate lobe, the anterior lobe of the pituitary gland, or a combination of these.

BRIEF DESCRIPTION OF THE DRAWINGS

The following exemplary drawings illustrate preferred embodiments of the invention. Other objects and features will be apparent from the following description and drawings in which the following figures disclose as follows:

FIG. 3 The catheter of FIG. 1, showing, within it: i) its action member 5 and ii) its steering system 6 with its distal end connected to the distal end of the catheter; and showing on its distal end: i) its collar deflated 10, ii) its malleable cushion 8 with an annular radiopaque and electro-stimulating ring 7 about it, and iii) its elastic, stretchable and radiopaque annular cuff 9 around a distally-extending central opening that is in communication with the opening in the distal end of the catheter, through distally-extending central openings (not shown) in the collar 10 and cushion 8.

FIG. 4 The catheter of FIG. 3, showing its distal end moved adjacent the medial wall of the sinus cavernosus with: i) its collar 10 deflated and ii) its cushion 8 in contact with the medial wall 11 of the sinus cavernosus.

FIGS. 5 and 6 the catheter of FIG. 4, showing: i) its collar 10 distally subsequently inflated against the medial wall 11 of the sinus cavernosus and ii) its cushion 8 then moved proximally towards the medial wall 11 of the sinus cavernosus.

FIG. 7 The catheter of FIGS. 5 and 6, showing: i)) its collar 10 distally inflated against the medial wall 11 of the sinus cavernosus and ii) its cushion 8 subsequently moved distally against the medial wall of the sinus cavernosus by applying suction to the proximal end of the catheter to suck venous blood out of the space 12 between the distal end of the catheter and the medial wall 11 of the sinus cavernosus through the central openings in the collar 10, cushion 8 and elastic cuff 9 of the catheter.

FIG. 10 The catheter of FIG. 7 showing: i) its cushion in contact with the medial wall of the sinus cavernosus and ii) an endovascular action member 15 extending outwardly of the distal end of the catheter and through the central openings in its collar, cushion and cuff and then through a perforation in the medial wall of the sinus cavernosus to the pituitary gland. for subdural treatment thereof.

FIG. 11 The catheter of FIG. 10, showing: i) its cushion moved away from the medial wall of the sinus cavernosus and ii) the endovascular action member 15 extending distally through the catheter and its collar, cushion and cuff and outwardly of the opening in the distal end of the catheter and through the central openings in its collar, cushion and cuff and then through a perforation in the medial wall 11 of the sinus cavernosus to the pituitary gland 16 for subdural treatment thereof.

DETAILED DESCRIPTION OF THE INVENTION

Figure 1:
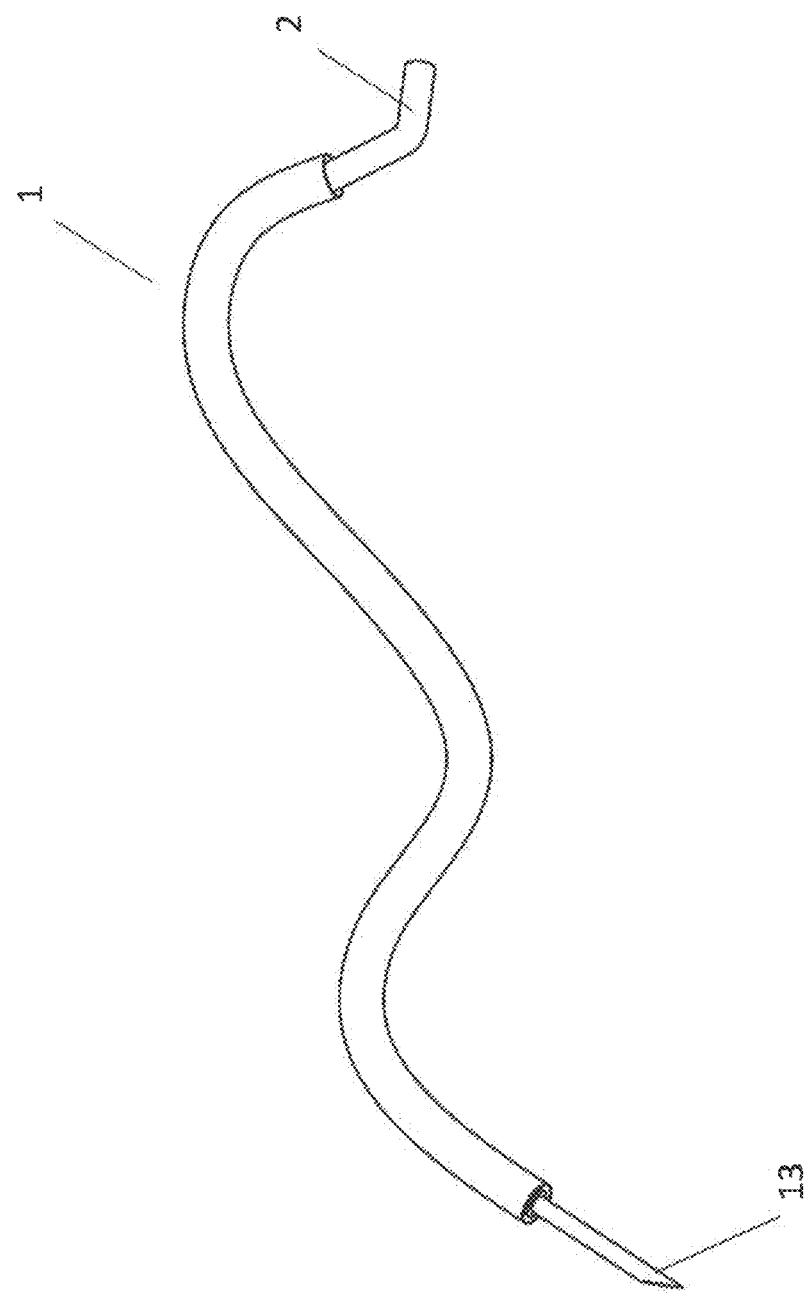
FIG. 1 A schematic illustration of a preferred embodiment of this invention: flexible catheter 1 containing a flexible guide wire 2 and having an opening at its distal end, through which the guide wire extends distally.
Figure 2:
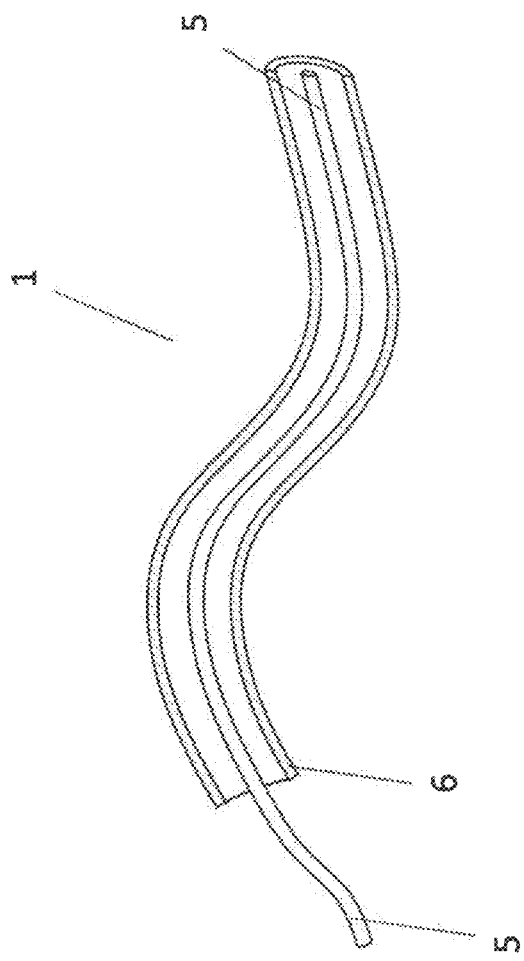
FIG. 2 The catheter of FIG. 1, showing, within it: i) an action member 5, e.g., an electrode or a microcannula, with its distal end in communication with the opening in the distal end of the catheter and ii) a guide wire steering system 6 with its proximal end connected to the proximal end of the catheter.

Herein, the term "an action member" preferably means one or more electrodes or one or more microcannulas or one or more push wires or any or some or all of them within a catheter.

Also herein, the term "guide wire" preferably means a tiny elongated wire designed to navigate a vessel to reach a segment of the vessel. Once the tip of the wire arrives at its destination, it acts as a guide that a larger catheter can rapidly follow for easier delivery to the destination. Such wires are characterized by their pushability, steerability, torque and opacity.

Pushability is the amount of force needed to advance the wire. Steerability is the ability and responsiveness of the wire tip to navigate vessels. Torque is the response of the wire to turning by the operator when navigating vessels. Opacity is its level of visibility under fluoroscopic imaging.

Also herein, the term "catheter" preferably means an elongated hollow flexible tube, made from a medical grade material, for insertion into a vessel. The tube makes it easier to enter the vessel and move within it with other devices or instruments, such as lasers, stents, and balloons for angioplasty.

Also herein, the term "microcannula" preferably means an elongated thin tube, the distal end of which can penetrate one or more cells of a mammalian patient. A microcannula with a capillary tube has a bore thin enough to deliver a minute drop of a liquid to a single cell penetrated by the microcannula and thereby treat, e.g., stimulate, the single cell or multiple cells by allowing injected fluid to diffuse among the cells. A microcannula which is not a capillary tube can be used to hold a movable push wire and/or provide air pressure for inflation/deflation, an anchoring foam, and/ or other elements to manipulate elements at the distal end of the catheter. Each microcannula can be extended through the elongated hollow tube of the catheter and subsequently retracted from the catheter through its elongated hollow tube.

Also herein, the term "distal end" preferably means the portions of a catheter or any of its action members at their distal extremities and their parts adjacent their distal extremities.

Also herein, the terms "mammalian patient" and "mammal" are used interchangeably and preferably mean a human or mammalian animal, such as a dog, particularly a human, in need of treatment.

Also herein, the term "femoral vein" preferably includes the inferior margin of the inguinal ligament which is known as the external iliac vein and is below the inguinal ligament.

Also herein, the term "endocrinological medical condition" preferably means a problem related to the components of the endocrine system, such as the adrenal glands, pituitary gland, and hypothalamus, including hypoglycemia, diabetes type I and II, obesity, hyperthyroidism, hypothyroidism, amenorrhea, dysmenorrhea, infertility, impotence, anorgasmia, delayed orgasm, perimenstrual syndrome, hypercholesterolemia, hypertriglycridinemia, Cushing's disease, Addison's disease, Addison's crisis, malabsorption syndrome, dysautonomia, chronic fatigue syndrome, fatigue, heat exhaustion, cold extremities, hot flashes, vasomotor instability, Raynaud's syndrome, hormonal disorders, metabolic disorders such as gout, disorders of metabolism and metabolic storage diseases where there is an accumulation of abnormal amounts of various substances such as glycogen in glycogen storage diseases, iron in hemochromatosis or copper in Wilson's disease, auto-immune disorders, sleep disorders and disruptions in the circadian rhythm. In particular the present invention relates to the treatment of Adison's disease and Adison's crisis, as well as pain, pain perception, post-traumatic stress disorder, depression and anxiety.

Figure 20:
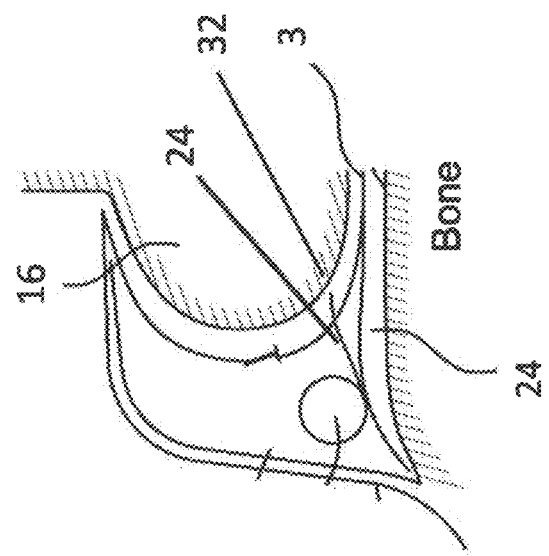
FIG. 20 The catheter of FIG. 19 showing: the endovascular electrode 24 of FIG. 14 then moving distally, from the distal end of the catheter, then moving through the medial wall of the sinus cavernosus and then extending through an opening in the medial wall of the sinus cavernosus to either just beneath the pituitary gland for subdural treatment thereof or inserted in the surface of the pituitary gland for epidural treatment thereof.

The system of this invention, as shown in FIGS. 1-12, provides electrical pulses and/or therapeutic or diagnostic liquids to a pituitary gland of a mammalian patient or to a pituitary stalk or to a hypothalamus of the mammalian patient directly or indirectly (i.e., subdurally) as shown in FIGS. 10 and 11 or indirectly (epidurally), i.e., about or adjacent or beneath or above the pituitary gland, pituitary stalk or the hypothalamus as shown in FIG. 20. The system uses a catheter 1 that has a distal end movable distally through one or more blood vessels of an endovascular route of the mammal. Through the catheter, one or more action members 5 or 15, preferably one or more electrodes 5 or 15 or one or more microcannulas 5 or 15 or one or more push wires 13 or any or some or all of them may be inserted, a distal end of each of which is movable distally within the catheter 1 and, via the catheter, through the endovascular route and then into and through the sinus cavernosus of the mammal.

The system preferably comprises an electrode array is provided for interfacing with the organ tissue in situ, the device comprising: a. a deformable array of electrodes comprising a plurality of electrodes in electrical communication with a plurality of deformable electrical interconnects and a connector line; wherein the deformable array of electrodes provides a net bending stiffness of the array low enough that the device is capable of establishing conformal contact with the tissue in situ; and b. a connection plug provided at the proximal end of the connector line of the electrode array provided with a distal end of which can be attached to a bone adjacent the organ, such an anterior wall of the sphenoid sinus/vomer, and a proximal end of which can be reversibly connected electrically to a wire that is connected electrically to a source of electrical stimulation for the organ.

The catheter 1 of the system shown in FIGS. 1-12 contains one or more microcannula or electrodes 5 or 15, as action members, extending through its elongated hollow tube. At least one of the action members has a distal end that can move:

distally within the catheter, through the endovascular route and then into and through the sinus cavernosus; and then distally out of the catheter, through an opening in the distal end of the catheter and then through a perforation in the medial wall of the sinus cavernosus to the pituitary gland and then to and into the pituitary gland, preferably when the distal end of the catheter is adjacent the medial wall of the sinus cavernosus.

The catheter 1 of the system shown in FIGS. 1-12 can also contain, in its elongated hollow tube, one or more additional microcannula 5 or 15, through which can be provided a movable push wire 13 and/or air pressure for inflation/deflation (e.g., of the collar 10 or a stabilizing device 28), an anchoring foam 17, and/or other elements to manipulate elements at the distal end of the catheter, such as the collar 10 or the ring 7. Alternatively, the push wire 13, air pressure for inflation/deflation, an anchoring foam, or other elements to manipulate elements at the distal end of the catheter can be provided directly through the elongated hollow tube of the catheter, Preferably, the push wire 13 has a distal end that can move:

distally, within an additional microcannula 5 or 15 in the catheter, through the endovascular route and then into and through the sinus cavernosus; and then distally out of the additional microcannula and the catheter through an opening in the distal end of the catheter and then through the perforation in the medial wall of the sinus cavernosus.

The distal end of the push wire 13 preferably has a tip 14 with a sharp, preferably pointed, distal element 14 that can be projected distally, through the opening in the distal end of the catheter, to perforate the medial wall of the sinus cavernous. Also preferably, the tip of the catheter has one or more conventional sensors or a Doppler probe to allow identification of cranial nerves or arteries.

Preferably, the elongated hollow tube of the catheter 1 of the system also contains a flexible guide wire 2, preferably with a blunt and atraumatic distal end, to guide the catheter through the endovascular route and and then into and through the sinus cavernosus. The distal end of the guide wire can be provided with a Doppler probe to identify the carotid artery and/or with an electrical stimulation device for identification of the abducens nerve.

Preferably, one or more action members of the catheter 1 of the system are located within the elongated hollow tube of the catheter. A conventional catheter 1 containing one or more conventional microcannula 5 or 15 can be used in this system. Each microcannula can: i) contain an electric wire for carrying a pulsed current to an electrode 5 or 15 (not shown) at the distal end of the catheter for providing electrical stimulation, at the distal end of the catheter or ii) carry a diagnostic or therapeutic liquid to the distal end of the catheter. Preferably, the microcannula for carrying a diagnostic or therapeutic liquid is a microcannula with a capillary tube. Also preferably, the distal end of each electrode has one or more contact points for electrical stimulation of endocrine tissue of the pituitary gland, the pituitary stalk or the hypothalamus. Also preferably, the distal end of each microcannula for a liquid has one or more side openings which are in communication with the microcannula's central hollow channel and through which:

small volumes of a fluid or gel can flow from a microcannula into the pituitary gland, the pituitary stalk or the hypothalamus, still more preferably with side openings that can be opened and closed by remote control; and/or small volumes of a pressurized gas can flow from a microcannula into the collar 10 to inflate it, so that distal surfaces of the collar are projected distally from the distal end of the catheter around a perforation in the medial wall of the cavernous sinus to close a space around the opening in the distal end of the catheter between the distal end of the catheter and the perforation, preferably before the tip of the push wire is projected distally from the opening in the distal end of the catheter to form the perforation in the medial wall of the cavernous sinus.

Also preferably, an annular radiopaque collar or ring 7 is provided on a distal part of the exterior of the tubular wall of the catheter 1 of the system, spaced away from the distal end of the catheter. The ring 7 allows the position of the distal part of the catheter to be identified with X-ray, MRI or CT-scan.

Also preferably, the distal end of the tubular wall of the catheter 1 of the system holds a cushion 8 that allows the distal end of the catheter to have good, preferably liquid tight, contact with the surface of the medial wall of the sinus cavernosus and thereby prevent venous blood from the cavernous sinus leaking into the sella or in or around the pituitary gland. The exterior of the distal end of the catheter, adjacent to, and proximal of, the cushion 8, is preferably provided with the radiopaque ring 7. Within the cushion 8 is preferably a central stretchable, elastic cuff 9, which at rest closes the opening in the distal end of the catheter 1, but can be stretched to allow movement, through its full diameter, of the push wire, 13 and/or subsequently a sealing plug or the anchoring foam 17. In this regard, the sharp tip 14 of the push wire 13 can be projected distally from the distal end of the catheter, through the opening, in the cushion 8 to perforate the medial wall of the cavernous sinus, and subsequently to force the anchoring foam distally from the catheter into the perforation made by the sharp element to close the perforation.

Also preferably, the exterior of a distal part of the catheter 1 of the system, adjacent to, and proximal of, the ring 7, is provided with an inflatable collar 10, which is flush with the outer surface of the tubular wall of the catheter when deflated. The ring 7 is preferably between the collar 10 and the cushion 8.

Also preferably, a distal part of the catheter 1 of the system, preferably between the collar 10 and the cushion 8, contains one or more electromagnetic localizers (not shown) to facilitate proper positioning of the distal part in the patient. Each localizer is part of a tracking system, in which the localizer includes a transmitter and receiver coil array, enabling it to transmit electromagnetic signals and receive electromagnetic energy from a transmitter coil array. The transmitter coil can suitably be located in, or adjacent to, the patient and can generate an electromagnetic field to energize each localizer. Suitable localizers and tracking systems include, for instance, those described in U.S. Pat. No. 8,549,732 B2 and U.S. Pat. No. 9,717,442 B2.

Also preferably, the catheter 1 of the system includes an integrated steering system, such as a guide wire within the elongated hollow tube of the catheter for pivoting or steering the distal end of the catheter, preferably by remote control 6 at the proximal end of the catheter, in a desired direction for distal movement through the endovascular route and then into and through the sinus cavernosus. More preferably, the catheter has a conventional steering system which can actively bend the hollow tube of the catheter to a predetermined angle of no less than 75°. Yet more preferably, the catheter has an exterior lumen within the hollow tube of the catheter and an interior lumen within the exterior lumen. The exterior lumen contains a first steering mechanism, and the interior lumen contains a second steering mechanism, that the first and second steering mechanisms being operable to actively bend the hollow tube to a predetermined angle of at least 80°, more preferably at least 85°, yet more preferably at least 90°, when moving the distal end of the catheter along the endovascular route. Such a catheter steering mechanism is described, for instance, in U.S. Pat. Nos. 8,152,756 B2, 8,715,226B2 and US20050203413A1.

Figure 19:
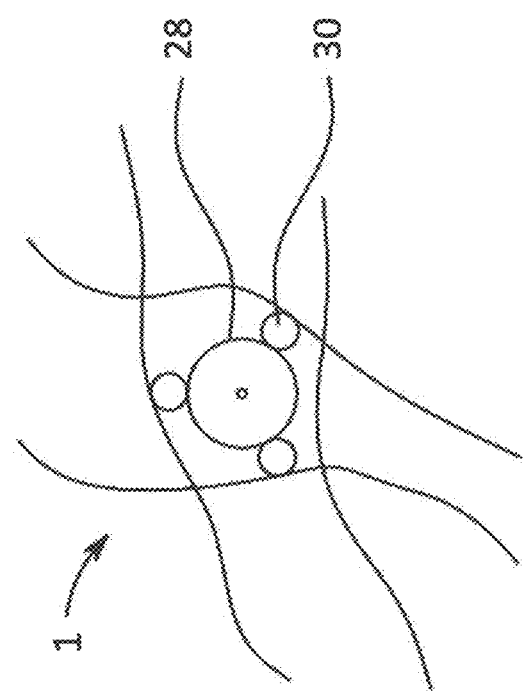
FIG. 19 A stabilizing device 28 on the exterior of the distal end of the catheter of FIG. 8 to secure the position of the distal end of the catheter within the perforation in the medial wall of the sinus cavernosus, without occluding the perforation.

Also preferably, the exterior of the distal end of the catheter 1 of the system, adjacent to, and proximal of, the inflatable annular collar, also has a stabilizing device 28, shown in FIG. 19, to secure the position of the distal end of the catheter within the perforation in the medial wall of the sinus cavernosus, without occluding the perforation. Preferably, the stabilizing device 28 comprises an inflatable tripod 29, provided circumferentially about the exterior of the catheter and having inflatable, radially extendable legs 30. Preferably, the stabilizing device 28 is connected to a source of air pressure (not shown), via a microcannula 5 or 15 or via the hollow tube of the catheter, which can inflate the legs 30 of the device.

Also preferably, distal portions of each electrode or microcannula 5 or 15 of the catheter 1 of the system have a form memory and thus can form a three-dimensional shape, such as a circle, oval or helix, within or about/around the pituitary gland, preferably when triggered by remote control. Still more preferably, distal portions of each electrode or microcannula, when inserted in the pituitary gland, have a coil shape within the pituitary gland.

Also preferably, a distal part of the catheter 1 of the system, particularly its hollow tube, has a conventional peel-away configuration (not shown), so that the catheter can be removed from a mammalian patient after it has been used to insert an electrode or microcannula 5 or 15 in the patient, so that the electrode or microcannula remains intact and properly positioned in the patient. A suitable peel-away configuration includes, for instance, those described in U.S. Pat. No. 7,697,996B2.

Figure 5:
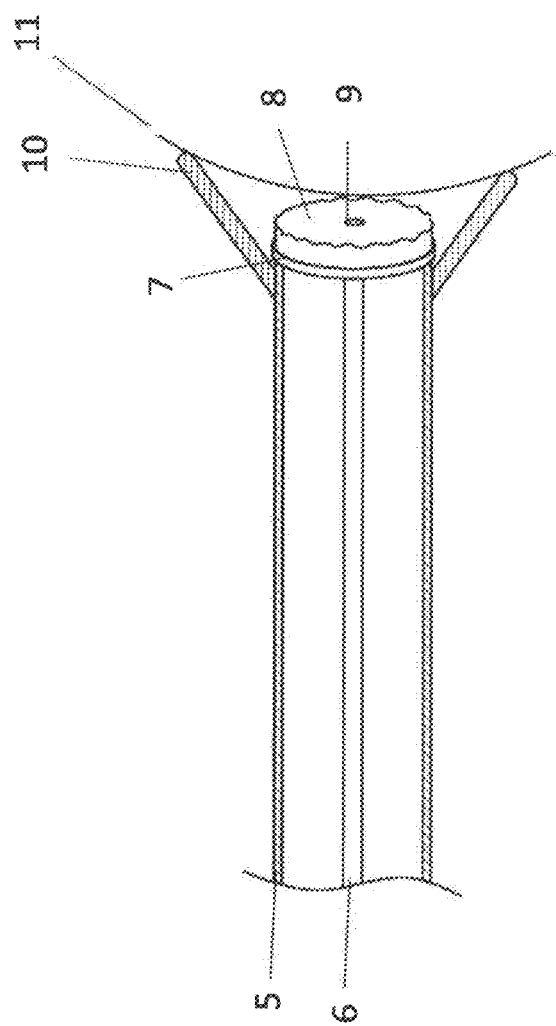
Figure 8:
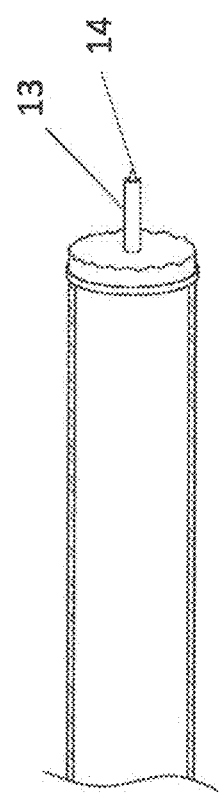
FIG. 8 The catheter of FIG. 3, showing a push wire 13 extending distally through the catheter and through the central openings in its collar, cushion and cuff and with a sharp, perforating tip at the distal end of the push wire; the tip extends distally out of the catheter through the central opening in the cuff, so that the tip can perforate the medial wall of the sinus cavernosus; the diameter of the push wire is smaller than the guide wire 2.
Figure 9:
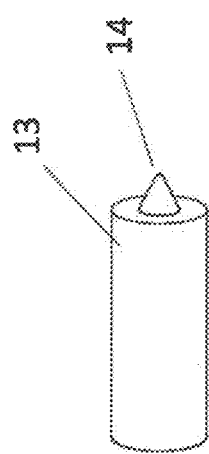
FIG. 9 The push wire of FIG. 8, showing its sharp, perforating tip at its distal end.
Figure 12:
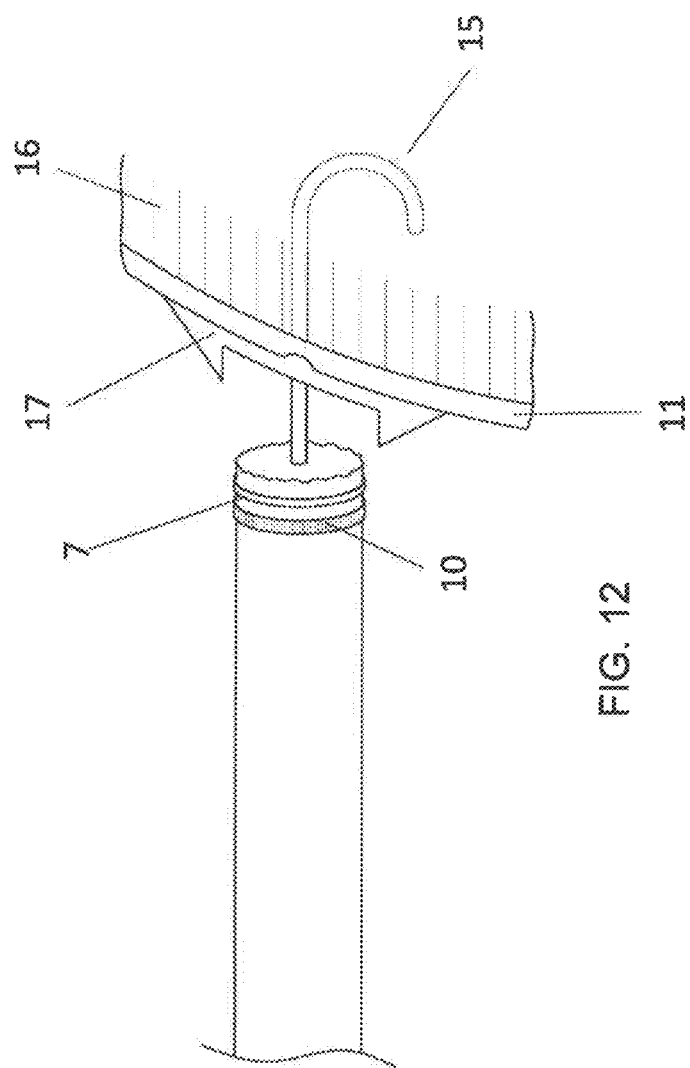
FIG. 12 The catheter of FIG. 11, showing an anchoring foam 17, used to seal the opening in the medial wall 11 of the sinus cavernosus around the endovascular action member 15 extending outwardly of the opening in the distal end of the catheter and through the central openings in its collar, cushion and cuff and then through the opening in the medial wall of the sinus cavernosus to the pituitary gland.
Figure 13:
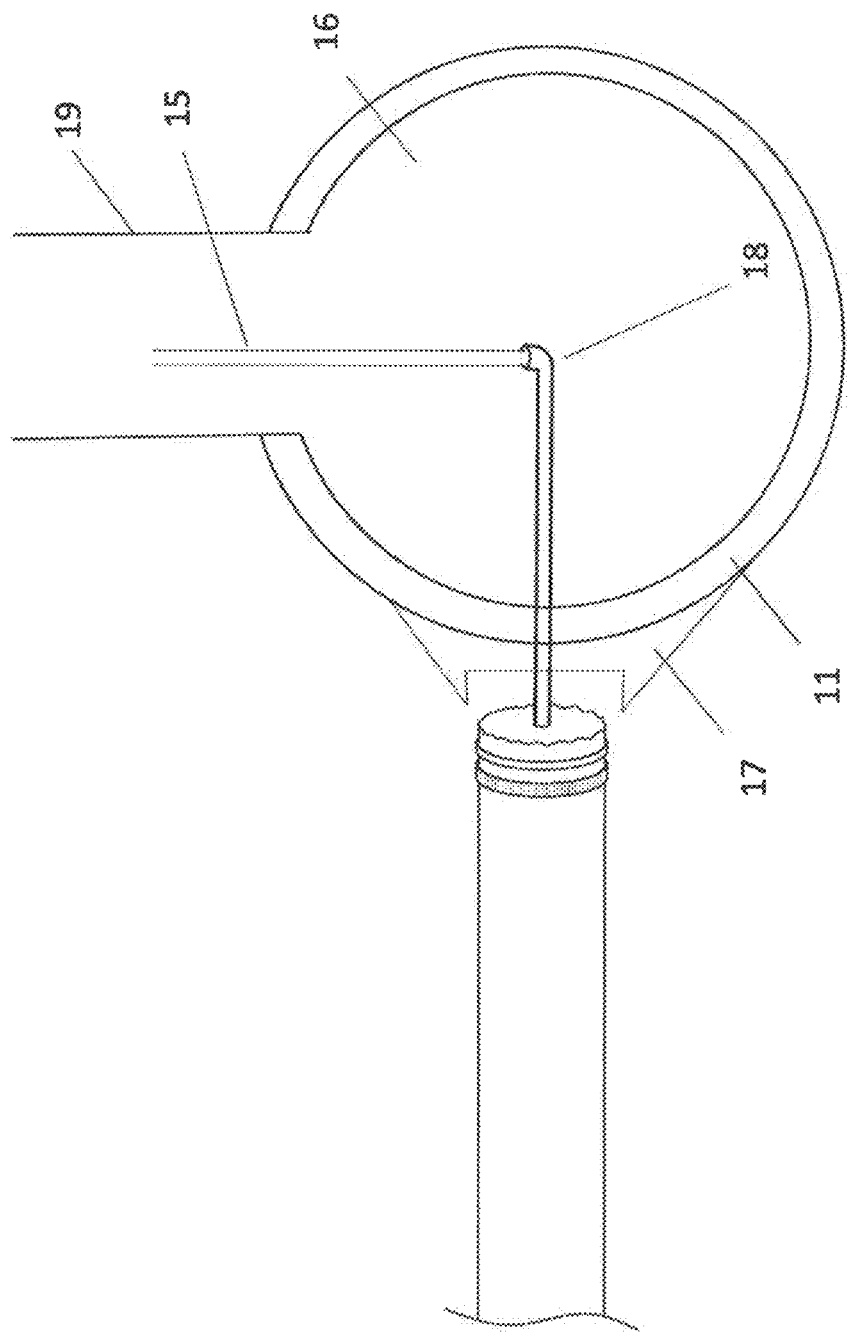
FIG. 13 The catheter of FIG. 12, showing the anchoring foam 17, used to seal the opening in the medial wall 11 of the sinus cavernosus around a second guiding catheter 18, releasing a further action member 15 extending upwardly of the opening in the distal end of the second catheter through the pituitary gland 16 into the pituitary stalk 19.
Figure 14:
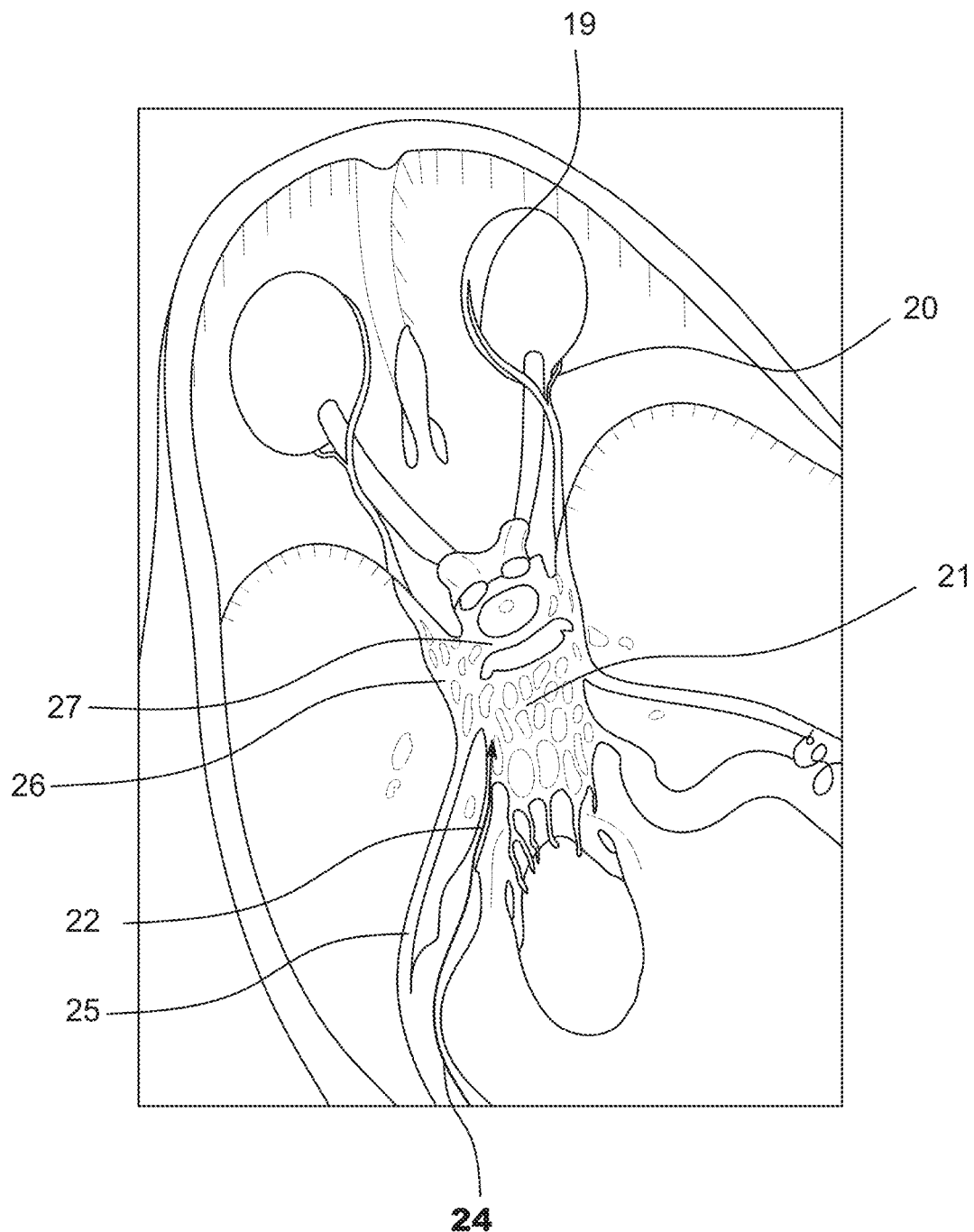
FIG. 14 The path of the distal end of an endovascular electrode 24, as an action member, that has been moved within the catheter of FIGS. 1 to 12 via the vena jugularis and then via the inferior or superior petrosal sinus to the sinus cavernosus.
Figure 15:
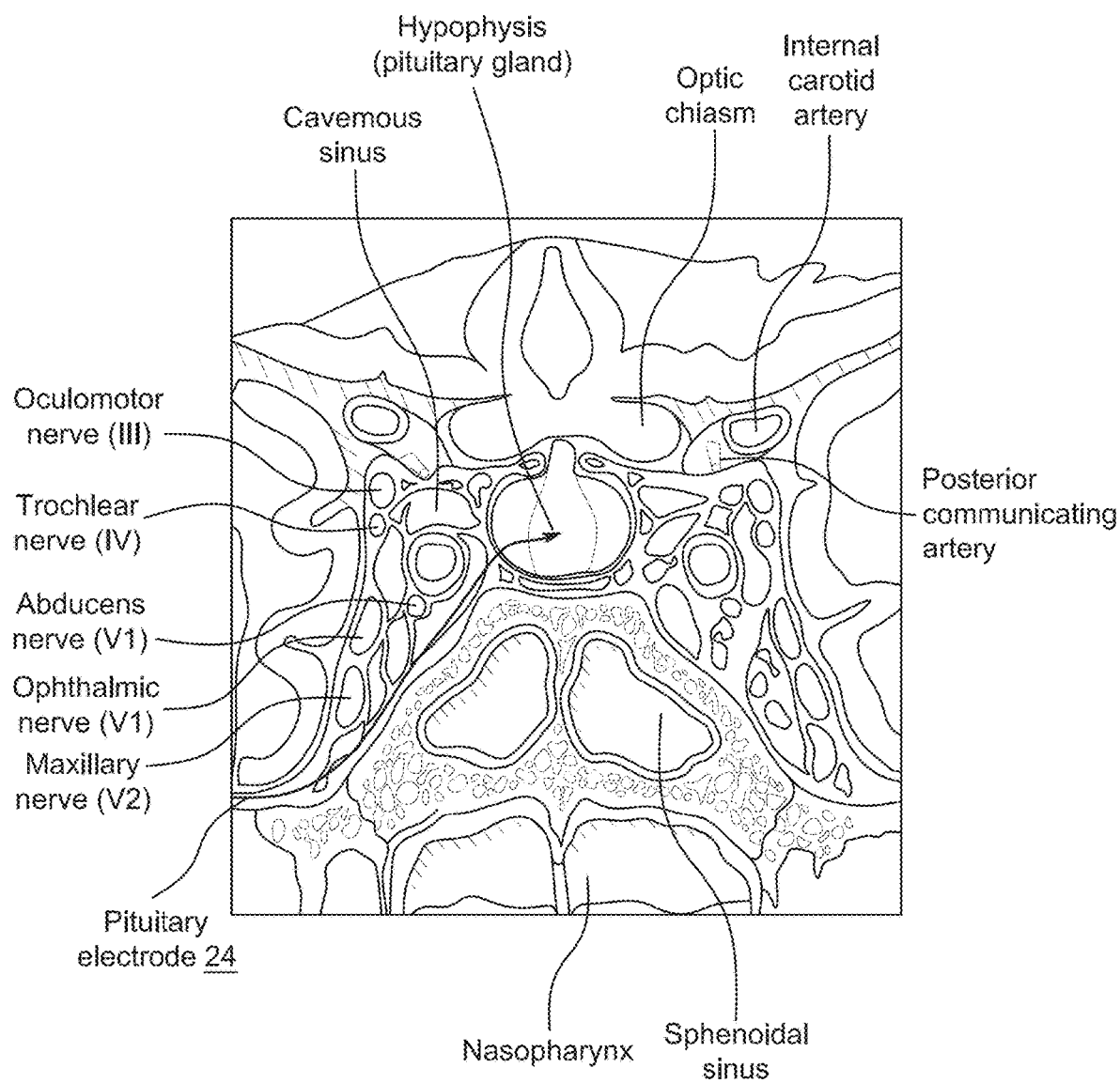
FIG. 15 The path of the distal end of the endovascular electrode 24 of FIG. 14 that has then been moved distally, from the distal end of the catheter, then moved through a perforation in the medial wall of the sinus cavernosus and then been inserted into the pituitary gland 16.
Figure 16:
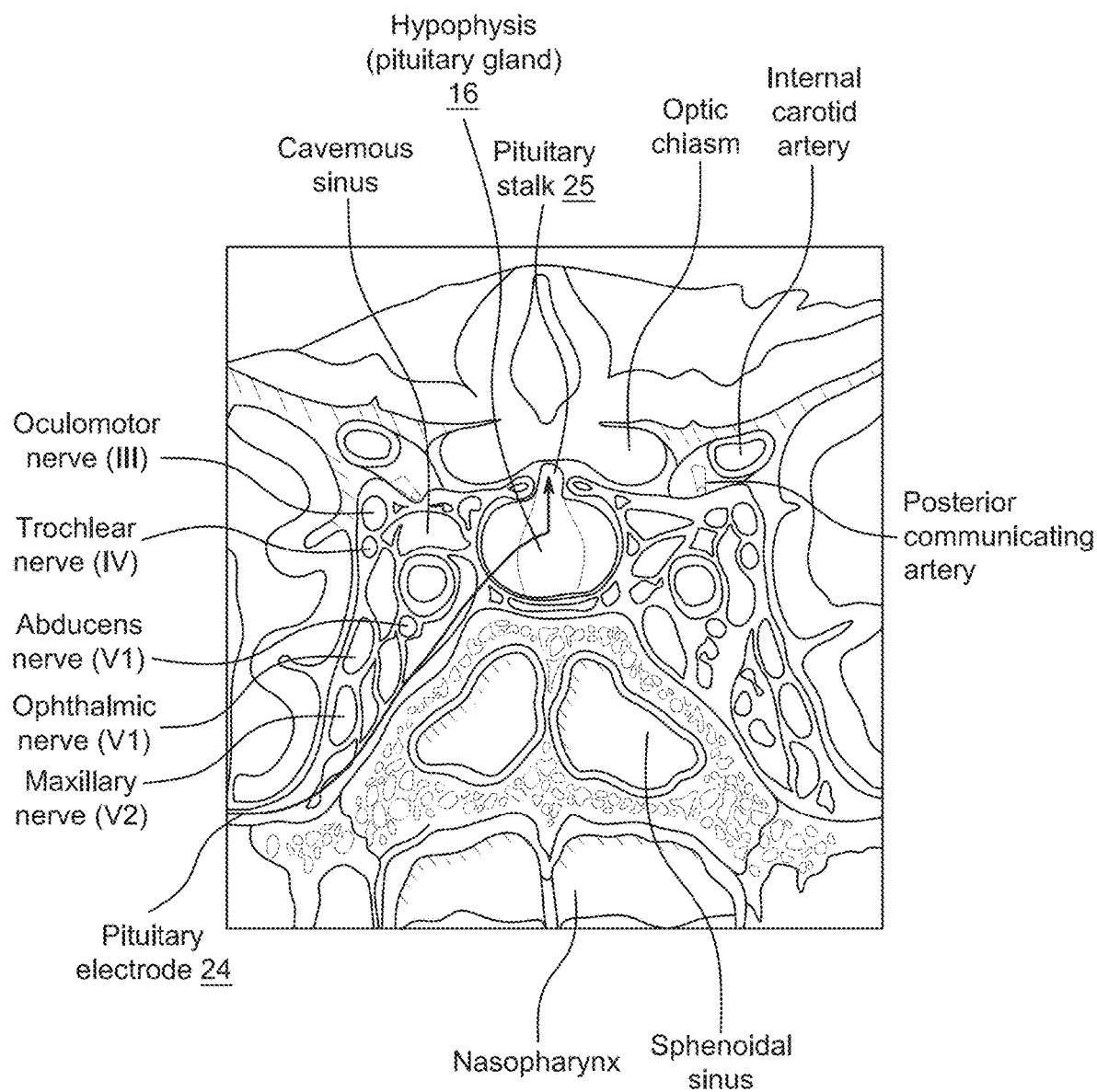
FIG. 16 The path of the distal end of the endovascular electrode 24 of FIG. 15 that has then been moved through the pituitary gland 16, then steered vertically and then inserted into, or parallel to, the pituitary stalk.
Figure 17:
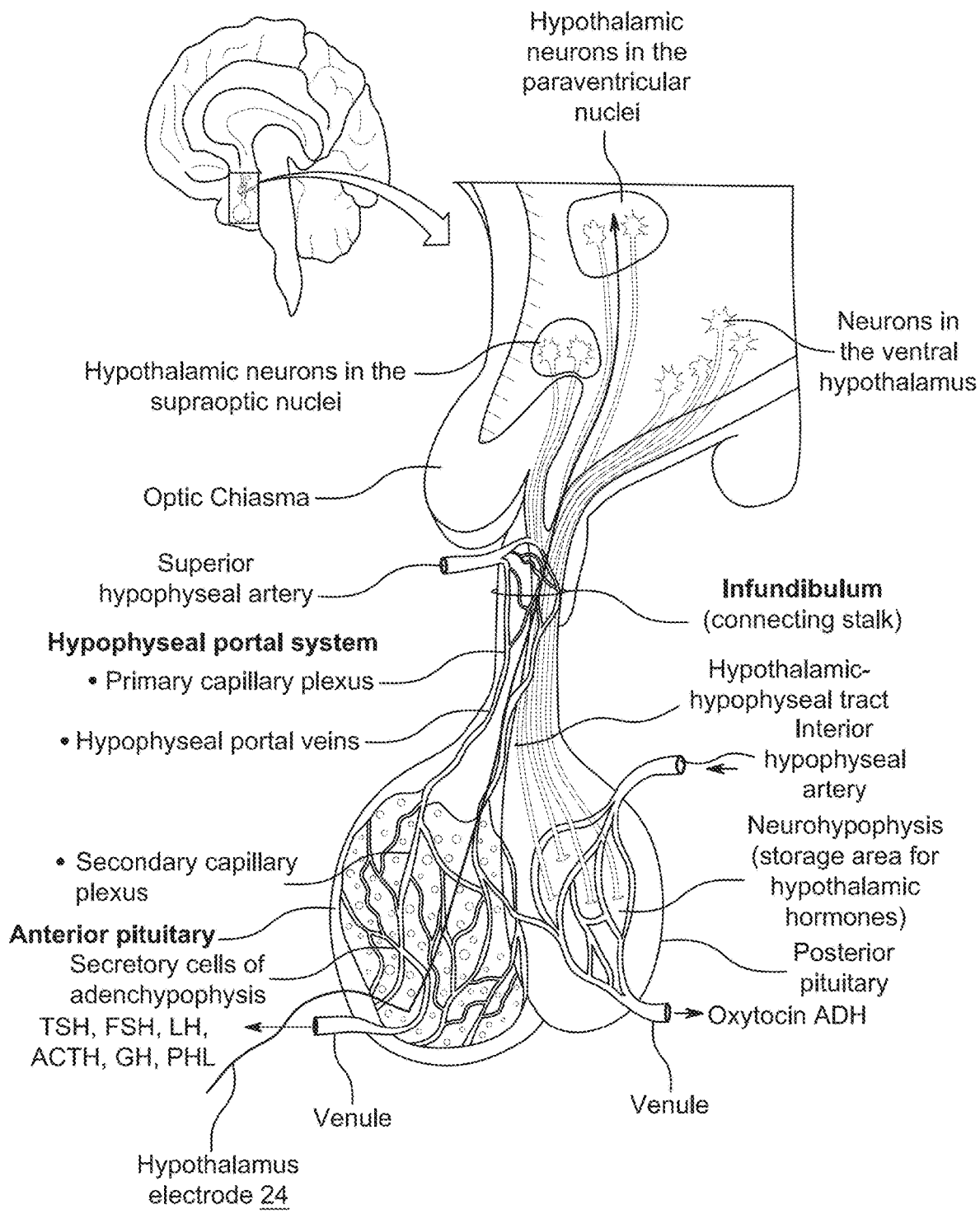
FIG. 17 The path of the distal end of the endovascular electrode 24 of FIG. 16 that has then been steered further vertically, then passed through, or parallel to, the pituitary stalk and then being inserted into the core of the hypothalamus.
Figure 18:
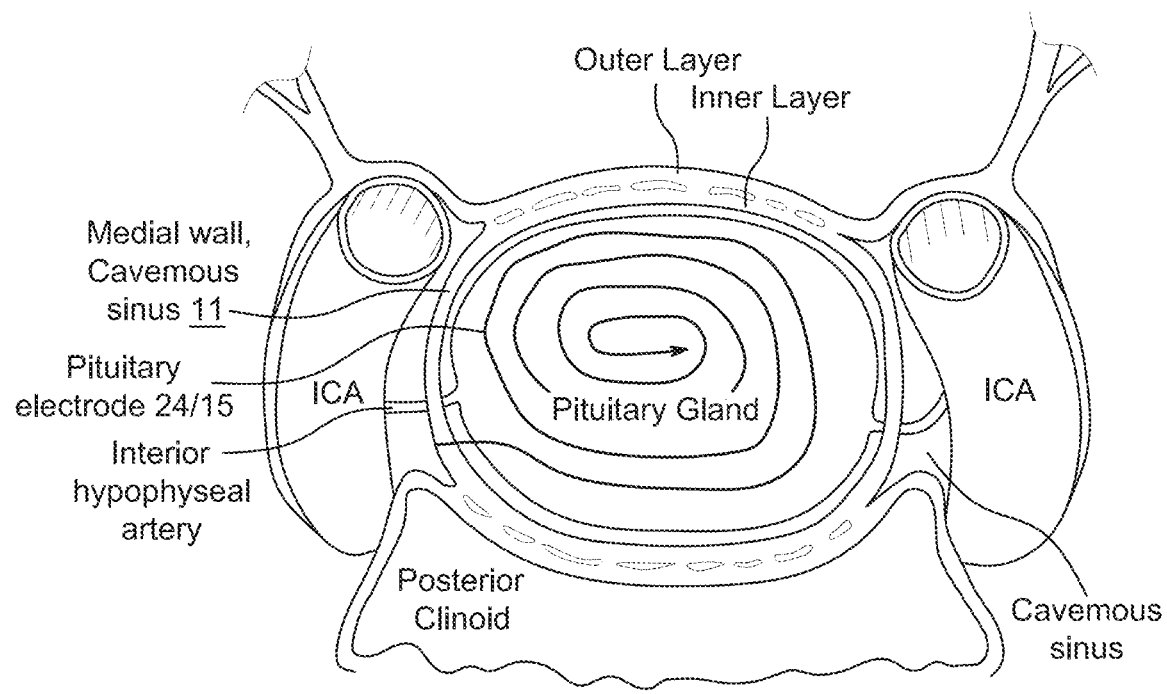
FIG. 18 The path of the distal end of the endovascular electrode 24 of FIG. 15 that has then formed a coil inside the pituitary gland 16.

Also preferably, the distal end of the catheter 1 of the system, containing one or more electrodes and/or one or more microcannulas 5 or 15, is moved through the endovascular route from the vena jugularis of the mammalian patient, then to the inferior or superior petrosal sinus of the mammal, and then to the sinus cavernosus of the mammal, where as shown in FIG. 14 are the superior ophthalmic vein 19, inferior ophthalmic vein 20, Basilar plexus 21, inferior petrosal sinus 22, jugular vein 23, endovascular pituitary electrode 24, superior petrosal sinus 25, cavernous sinus 26 and circular venous plexus 27. More preferably, the distal end of the catheter is moved through the endovascular route from the ileac vein or femoral vein in a groin of the mammal where the catheter has been inserted in the mammal. The distal end of an electrode or microcannula is then moved distally out of the catheter, through the opening in the distal end of the catheter, and through the medial wall of the sinus cavernosus and is then inserted subdurally into the pituitary gland 16 as shown in FIGS. 15 and 20 or positioned epidurally of the pituitary gland as shown in FIG. 20. In this regard, FIG. 20 particularly shows the trajectory of an electrode 24 being either epidurally placed adjacent a surface of the pituitary gland 16 (at 31) or subdurally inserted into the surface of the pituitary gland 16 (at 32). The distal end of the subdurally placed electrode or microcannula 5 or 15 can then be moved through the pituitary gland, then steered to move vertically and then inserted into the pituitary stalk as shown in FIG. 16. The distal end of the electrode or microcannula can then be steered further vertically, then passed through the pituitary stalk 25 and then inserted into the core of the hypothalamus as shown in FIG. 17. In this regard:

the catheter 1 can be pressed against the medial wall 11 of the cavernous sinus as shown in FIG. 4; thereby, the cushion 8 is pressed against the surface of the medial wall 11 of the sinus cavernosus;

the collar 10 can then be inflated as shown in FIGS. 5 and 6 to thereby seal off the space around the distal end of the catheter; inflation and deflation of the collar 10 can be done through a microcannula 5 or 15 or directly through the elongated hollow tube of the catheter;

to allow full contact of the cushion 8 at the distal end of the catheter with the medial wall 11 of the sinus cavernosus, the pressure in the sealed space 12 can then be reduced as shown in FIG. 7 by applying suction through a microcannula or through the catheter; thereby, the medial wall 11 of the cavernous sinus is pulled against the cushion 8 to provide full contact between the two;

the medial wall of the cavernous sinus can then be perforated with the sharp pointed tip 14 of the push wire 13 shown in FIGS. 8 and 9; in this regard, the tip 14 is preferably shallow, e.g., only 1 mm long, so if the wall of the carotid artery is accidently touched, the tip will not cause full thickness injury of the carotid wall.

a pituitary electrode or microcannula 5 or 15 can then be inserted, via the catheter into the pituitary gland 16 as shown in FIGS. 10 and 11 for subdural treatment of the pituitary gland or alternatively under or around the pituitary gland for epidural treatment of the pituitary gland as shown in FIG. 20. Because the pressure in the sealed space 12 has been reduced, the medial wall 11 of the cavernous sinus continues to adhere to the cushion 8 at the distal end of the catheter;

when the pressure in the sealed space 12 is subsequently allowed to normalize, the medial wall 11 of the cavernous sinus takes its normal anatomical position, which allows some space between it and the cushion 8; therefore, the sealed space 12 can then be filled with an anchoring foam 17, supplied by an additional microcannula 5 or 15, as shown in FIG. 13 or directly through the elongated hollow tube of the catheter to form a cast of the sealed space 12; the anchoring foam may then also seep through the perforation of the medial wall 11 of the cavernous sinus 17;

the collar 10 can be deflated and the catheter 1 can be pulled away from the medial wall 11 of the cavernous sinus, leaving the electrode/microcannula 5 or 15 fixed in place by the anchoring foam 17 and safely inserted into/around/under the pituitary gland 16; the anchoring foam 17 effectively sealing the medial wall of the cavernous sinus, preventing venous blood of the cavernous sinus to seep in the space between medial wall 11 and pituitary gland 16; and then a stabilizing device 28 as shown in FIG. 19, on the exterior of the distal end of the catheter 1, can be used to secure the position of the distal end of the catheter within the perforation in the medial wall of the sinus cavernosus, without occluding the perforation; preferably, the stabilizing device 28 includes an inflatable tripod 29, provided circumferentially about the exterior of the catheter and having inflatable, radially extendable legs 30.

The catheter 1 of this invention can provide electrical pulses and/or therapeutic or diagnostic liquids directly to a pituitary gland of a mammal or to a pituitary stalk or to a hypothalamus of the mammal via the pituitary gland. The catheter contains one or more, conventional action members, a distal end of each of which can be moved in a conventional manner distally within the catheter through one or more blood vessels of the mammal and then via a sinus cavernosus of the mammal to a medial wall of the cavernous sinus. The catheter features:

an action member that is a push wire, a distal end of which has a tip with a sharp, preferably pointed, element that can be projected distally from an opening in the distal end of the catheter to form a perforation in the medial wall of the cavernous sinus, through which perforation the distal end of one or more other action members, preferably one or more electrodes and/or microcannulas, can be moved distally through the cavernous sinus and the one or more other action members can then be inserted in the pituitary gland from the distal end of the catheter.

Preferably a distal-most part of the catheter includes a malleable cushion to allow good contact of the distal-most part with the surface of the medial wall of the sinus cavernosus. Also preferably, the exterior of the distal end of the catheter, adjacent to, and proximal, of the cushion contains an annular collar that can be inflated, so that distal surfaces of the collar are projected distally from the distal end of the catheter around the perforation in the medial wall of the cavernous sinus to close a space around the opening in the distal end of the catheter between the distal end of the catheter and the perforation, preferably before the tip of the push wire is projected distally from the opening in the distal end of the catheter to form the perforation in the medial wall of the cavernous sinus. Also preferably, the exterior of the distal end of the catheter, preferably between the collar and the cushion, is provided with a ring that contains a radiopaque marking that can be recognized by X-ray, fluoroscopy, angiogram, MRI or a CT-scan. Also preferably, the distal end of the catheter can be pivoted or steered in a desired direction, preferably by remote control, for controlling its distal movement through the endovascular route and then into and through the sinus cavernosus.

The method of this invention provides electrical pulses and/or therapeutic or diagnostic liquids directly to a pituitary gland of a mammal or to a pituitary stalk or to a hypothalamus of the mammal via the pituitary gland, comprising the steps of:

moving a distal end of a catheter that contains one or more action members, preferably, preferably one or more electrodes and/or microcannulas, a distal end of each of which is movable distally within the catheter, through an endovascular route of the mammal route from the vena jugularis of the mammal, to the inferior or superior petrosal sinus of the mammal, and then to the sinus cavernosus of the mammal; and then forming a perforation in the medial wall of the cavernous sinus to the pituitary gland; and then moving the distal end of each of the one or more action members distally from the catheter through an opening in the distal end of the catheter and then through the perforation in the medial wall of the sinus cavernosus, to the pituitary gland, preferably when the distal end of the catheter is adjacent the medial wall of the sinus cavernosus.

Preferably, the distal end of the catheter moves via one or more blood vessels of an endovascular route from the ileac vein or femoral vein in a groin or the cephalic vein in the arm of the mammal where the catheter is inserted in the mammal.

With this system, its catheter and its method, one or more electrodes 5 or 15 can be connected to a subcutaneous pulse generator and/or one or more microcannulas 5 or 15 can be connected to a source of a therapeutic liquid, such as a pump and reservoir for regulatory hormones or proteins, RNAs, stem cells, cells that produce therapeutic substances, viruses, cells that can modify native pituitary gland cells and pharmaceutical compositions/drugs, and each electrode and/or microcannula can be implanted more safely in the pituitary gland, the pituitary stalk or the hypothalamus of a mammal patient for temporary or permanent stimulation thereof. In this regard, endovascular access to the basic core of the brain in accordance with this invention is simpler than via the cerebral cortex and safer and easier than via the sinus sphenoidalis. By treating the pituitary gland in this way with electrical pulses and/or therapeutic liquids, it is believed that: pituitary functions could be stimulated or inhibited, as desired, and problems of infertility, epilepsy, morbid obesity, and type II diabetes could be treated; and symptoms and diseases of the pituitary gland (e.g., Cushing's disease or Growth Hormone deficiency), as well as general disorders (type II diabetes, adipositis and infertility) in which the pituitary gland is involved, could be treated.

In particular, the distal end of each of the one or more electrodes 5 or 15 can be used to electrically stimulate the anterior and intermediate lobe of the pituitary gland to produce and secrete ACTH and/or MSH. The distal end of each electrode can also be used to electrically stimulate the posterior lobe of the pituitary gland and thereby stimulate the magnocellular nuclei (i.e., the supraoptic and paraventricular nuclei) of the anterior hypothalamus through axons that descend through the pituitary stalk to the posterior lobe of the pituitary gland. The present invention also relates to a method for spatial and temporal electrically interfacing with an organ, preferably brain tissue, more preferably the pituitary gland, the method comprising the steps of: providing an electrode array according to the invention, and electrically contacting at least a portion of the plurality of electrodes with the tissue by conformally contacting a surface of the tissue with the electrode array; and spatio-temporally interfacing the brain tissue with the conformable device to monitor or actuate a spatio-temporal profile over the surface of the brain tissue in electrical contact with the plurality of electrodes; and actuating electrical activity over the brain surface by applying an electric potential of a plurality of individual brain surface locations beneath each electrode of the array of electrodes at a plurality of different locations and/or time points; and/or optionally, monitoring the spatio-temporal electrical brain profile with the device in conformal and electrical contact with a brain surface of a subject, wherein the monitoring comprises detecting an electric potential of a plurality of individual brain surface locations beneath each electrode of the array of electrodes at a plurality of different time points.

Moreover, electrical activity of a patient's pituitary cells and pituitary functions of a patient can be continuously measured and controlled via an electrode implanted in the pituitary gland and connected to a controller implanted subcutaneously in the patient. Likewise, the pituitary stalk or the hypothalamus could be treated with electrical pulses and/or therapeutic liquids or their functions could be continuously measured and controlled. Moreover, a catheter can be provided having an electrical stimulating device at its distal end which can be used for: i) identification of cranial nerves, particularly the abducens nerve; this can be done by EMG (electrode near or in the eye), or the patient indicating symptoms (diplopia); and ii) identifying the carotid artery, for instance by measuring temperature, oxygenation, flow, pulsations or by echo doppler.

The present invention also relates to a method of alleviating an endocrinological condition in a patient suffering therefrom, the method comprising the steps of:
placing an electrode in electrical contact with the pituitary gland;
detecting a bodily activity or a physiological change (e.g., temperature or heart rate) associated with the endocrinological condition; and
activating the electrode to initiate application of an electrical signal to the pituitary gland, or adjusting application of an electrical signal to the pituitary gland in response to alleviate the patient's endocrinological disorder.

In this regard, electrical stimulation of the pituitary gland by the electrode can be used to treat the following indications:

| Pituitary Gland | Treatment | Indication |
| --- | --- | --- |
| Anterior lobe | Decrease ACTH Production | M. Cushing |
| Anterior lobe/ intermediate lobe | Increase ACTH Production | Secondary adrenal insufficiency |
| | Increase ACTH Production | Pituitary insufficiency |
| | Increase ACTH/alfa MSH Production | Auto immune disorders |
| | Modification ACTH production | Depression |
| | Decrease PRL Production | Prolactinoma |
| | Modification FSH/LH Production | Poly Cystic Ovary Syndrome |
| Posterior lobe | Increase Oxytocin Production | Severe oncological pain |
| | Increase Oxytocin Production | Anxiety disorders and PTSD |

Preferably, the present invention also relates to a method for the intra-pituitary gland administration of a pharmacologically active agent inducing production of steroidal hormones in the adrenal glands of a mammalian patient, the method comprising transferring into/around the pituitary gland a pharmaceutical preparation comprising an effective concentration of the pharmacologically active component through a microcannula as disclosed herein above. Preferably the active agent comprises a corticotropin-releasing hormone (CRH) or analogue thereof, or any other suitable agent including peptides and/or oligonucleotides.

The present invention also relates to a system and method in which a distal end of an electrode array is implanted, preferably permanently, in an organ, preferably brain tissue, such as a pituitary gland, of a mammalian patient for intermittent electrical stimulation thereof and a proximal end of the electrode is provided with a connection plug, a distal end of which can be attached to a bone adjacent the organ, such an anterior wall of the sphenoid sinus/vomer, and a proximal end of which can be reversibly connected electrically to a wire that is connected electrically to a source of electrical stimulation for the organ.

Preferably the electrode array is provided for interfacing with the organ tissue in situ, the electrode array comprising:
a. a deformable array of electrodes comprising a plurality of electrodes in electrical communication with a plurality of deformable electrical interconnects and a connector line; wherein the deformable array of electrodes provides a net bending stiffness of the array low enough that the device is capable of establishing conformal contact with the tissue in situ; and b. a connection plug provided at the proximal end of the connector line of the electrode array provided with a distal end of which can be attached to a bone adjacent the organ, such an anterior wall of the sphenoid sinus/vomer, and a proximal end of which can be reversibly connected electrically to a wire that is connected electrically to a source of electrical stimulation for the organ.

Preferably, the method according to the invention comprises the steps of:
a. providing an electrode array as set out above, and i. electrically contacting at least a portion of the plurality of electrodes with the tissue by conformally contacting a surface of the tissue with the electrode array; and ii. spatio-temporally interfacing the brain tissue with the conformable device to monitor or actuate a spatio-temporal profile over the surface of the brain tissue in electrical contact with the plurality of electrodes; and iii. actuating electrical activity over the brain surface by applying an electric potential of a plurality of individual brain surface locations beneath each electrode of the array of electrodes at a plurality of different locations and/or time points; and iv. optionally monitoring the spatio-temporal electrical brain profile with the device in conformal and electrical contact with a brain surface of a subject, wherein the monitoring comprises detecting an electric potential of a plurality of individual brain surface locations beneath each electrode of the array of electrodes at a plurality of different time points.

Preferably, the stimulation and/or monitoring comprises treating and/or monitoring a patient suffering from an endocrinological medical condition. More preperably, the endocrinological medical condition comprises a problem related to the components of the endocrine system, such as the adrenal glands, pituitary gland, and hypothalamus, including hypoglycemia, diabetes type I and II, obesity, hyperthyroidism, hypothyroidism, amenorrhea, dysmenorrhea, infertility, impotence, anorgasmia, delayed orgasm, perimenstrual syndrome, hypercholesterolemia, hypertriglycridinemia, Cushing's disease, Addison's disease, Addison's crisis, malabsorption syndrome, dysautonomia, epilepsy, chronic fatigue syndrome, fatigue, heat exhaustion, cold extremities, hot flashes, vasomotor instability, Raynaud's syndrome, hormonal disorders, metabolic disorders such as gout, disorders of metabolism and metabolic storage diseases where there is an accumulation of abnormal amounts of various substances such as glycogen in glycogen storage diseases, iron in hemochromatosis or copper in Wilson's disease, auto-immune disorders, sleep disorders and disruptions in the circadian rhythm. In particular the present invention relates to the treatment of Adison's disease and Adison's crisis, as well as pain, pain perception, post-traumatic stress disorder, depression and anxiety.

The invention claimed is:
1. A system for providing electrical pulses and/or therapeutic or diagnostic liquids directly to a pituitary gland, a pituitary stalk, a hypothalamus, or other brain area of a mammalian patient via the pituitary gland, the system comprising:
- a catheter having a distal end comprising an opening, the catheter configured to be movable distally through blood vessels of an endovascular route of the patent, into and through a sinus cavernosus of the patient,
- the catheter comprising an action member comprising an electrode and/or a microcannula, wherein the action member is a push wire having a distal end configured to be moveable
  - (i) distally, within the catheter, through the endovascular route, into and through the sinus cavernosus, and
  - (ii) distally out of the catheter through the opening, through a perforation in a medial wall of the sinus cavernosus to the pituitary gland, and into or around the pituitary gland; and
- wherein the system is adapted to actively bend to a predetermined angle of from 30 to 120° when moving along the endovascular route.

2. The system of claim 1, comprising at least two action and/or steering members disposed in one or more working channels in an exterior lumen of the catheter and configured to actively bend or pivot the catheter to a predetermined angle of no less than 75°.

3. The system of claim 1, wherein the catheter comprises first and second annular wall components with an annular lumen disposed between the first and second annular wall components, and/or one or more working channels in a wall component of the catheter.

4. The system of claim 3, further comprising a secondary catheter for accessing the pituitary stalk located inside the catheter and operable to project distally from the catheter and actively bend or pivot a predetermined angle of no less than 75°.

5. The system of claim 1, wherein the catheter further comprises a tip with a sharp element adapted to be projected distally from the opening in the distal end of the catheter.

6. The system of claim 1, wherein the action member comprises a first guide wire for pivoting or steering the distal end of the catheter in a desired direction.

7. The system of claim 1, wherein a distal end of the catheter comprises an electromagnetic localizer having a transmitter and receiver coil array, the electromagnetic localizer configured to transmit electromagnetic signals and receive electromagnetic energy from a transmitter coil array.

8. The system of claim 1, comprising an electrode or electrode array having a distal end with one or more contact points for electrical stimulation of tissue of the pituitary gland, the pituitary stalk or the hypothalamus, the distal end of the electrode or electrode array adapted to electrically stimulate the pituitary gland to produce and secrete oxytocin.

9. The system of claim 8, wherein the electrode or electrode array comprises:
- (i) a deformable array of electrodes comprising a plurality of electrodes in electrical communication with a plurality of deformable electrical interconnects and a connector line, wherein the deformable array of electrodes is configured to provide a net bending stiffness of the array low enough such that the system establishes conformal contact with tissue in situ; and
- (ii) a connection plug at a proximal end of the connector line having a distal end adapted to attach to a bone adjacent an organ and a proximal end configured to be reversibly connected to a wire electrically connected to a source of electrical stimulation for the organ.

10. The system of claim 1, comprising a microcannula having a distal end with one or more central hollow channels, each channel having one or more side openings through which small volumes of a fluid or gel can flow into the pituitary gland, the pituitary stalk, or the hypothalamus.

11. The system of claim 1, wherein the electrode and/or the microcannula has a shape memory that is adapted to form a three-dimensional shape within or about the pituitary gland.

12. The system of claim 1, further comprising at least one of a subcutaneous pulse generator connectable to the electrode, and a pump and a reservoir connectable to the microcannula.

13. The system of claim 1, wherein an exterior of the distal end of the catheter comprises a radiopaque ring and/or a stabilizing device comprising an inflatable tripod.

14. A system for providing electrical pulses and/or therapeutic or diagnostic liquids directly to a pituitary gland, a pituitary stalk, a hypothalamus, or other brain area of a mammalian patient via the pituitary gland, the system comprising:
- a catheter having a distal end comprising an opening, the catheter configured to be moveable distally through blood vessels of an endovascular route of the patient, into and through a sinus cavernosus of the patient,
- the catheter comprising an action member comprising an electrode and/or a microcannula, the action member having a distal end configured to be moveable:
  - (i) distally, within the catheter, through the endovascular route, into and through the sinus cavernosus, and
  - (ii) distally out of the catheter through the opening, through a perforation in a medial wall of the sinus cavernosus to the pituitary gland, and into or around the pituitary gland,
- wherein the system is adapted to actively bend to a predetermined angle of from 30 to 120° when moving along the endovascular route, and
- wherein a distal-most part of the catheter comprises a cushion, and an exterior of the distal end of the catheter, adjacent to and proximal of the cushion, comprises a deployable annular collar with distal surfaces which are distally projectable from the distal end of the catheter and configured to enclose a volume around the distal end of the catheter around the perforation in the medial wall of the sinus cavernosus to close a space around the opening between the distal end of the catheter and the perforation.

15. A method for providing electrical pulses and/or therapeutic or diagnostic liquids directly to a pituitary gland, a pituitary stalk, a hypothalamus, or other brain area of a mammalian patient via the pituitary gland, the method comprising:
- providing the system of claim 1, the distal end of the catheter comprising one or more of an electrode or electrode array, a microcannula, and a guidance member;
- moving a distal end of the one or more of the electrode or electrode array, the microcannula, and the guidance member distally, within the catheter, through an endovascular route of the patient from a vena jugularis, to an inferior or superior postal sinus and to a sinus cavernosus;
- perforating a medial wall of the cavernosus sinus to the pituitary gland; and
- moving the distal end of the one or more of the electrode or electrode array, the microcannula, and the guidance member distally from the catheter, through the opening in the opening in the distal end of the catheter and through the perforated medial wall of the sinus cavernosus to the pituitary gland.

16. The method of claim 15, wherein the electrode or electrode array comprises:
   (i) a deformable array of electrodes comprising a plurality of electrodes in electrical communication with a plurality of deformable electrical interconnects and a connector line,
   wherein the deformable array of electrodes is configured to provide a net bending stiffness of the array low enough such that the system establishes conformal contact with tissue in situ; and
   (ii) a connection plug at a proximal end of the connector line having a distal end adapted to attach to a bone adjacent an organ and a proximal end configured to be reversibly connected to a wire electrically connected to a source of electrical stimulation for the organ; and
   wherein the method further comprises:
   electrically contacting at least a portion of the plurality of electrodes with the tissue by conformal contact with the tissue;
   spatially and temporally interfacing the tissue with the system to monitor or actuate a spatio-temporal profile over the tissue in electrical contact with the plurality of electrodes; and
   actuating electrical activity by applying an electric potential to the tissue beneath each electrode of the plurality of electrodes at a plurality of time points.

17. The method of claim 16, further comprising monitoring a spatio-temporal electrical profile with the system in conformal and electrical contact with the subject, wherein the monitoring comprises detecting an electrical potential of the tissue beneath each electrode of the plurality of electrodes at a plurality of different times points.

18. A method of alleviating an endocrinological medical condition in a mammalian patient, the method comprising:
   placing an electrode or electrode array in electrical contact with a pituitary gland of the mammalian patient with the system of claim 1;
   detecting activity associated with or of relevance to the endocrinological condition; and
   activating the electrode or electrode array to initiate application of an electrical signal to the pituitary gland, or
   adjusting application of an electrical signal to the pituitary gland in response to alleviate, repair, or prevent worsening of the endocrinological condition.

19. A method for intra-pituitary gland administration of a pharmacologically active agent inducing or inhibiting production of steroidal hormones in adrenal glands of a mammalian patient though a change of pituitary gland function, the method comprising:
   transferring, into the pituitary gland, a pharmaceutical preparation comprising an effective concentration of the pharmacologically active agent though the microcannula of the system of claim 1.

20. The method of claim 19, wherein the pharmacologically active agent comprises a corticotropin-releasing hormone (CRH), analogue thereof, or combinations of CRH with other pharmacologically active components.

* * * * *